United States Patent [19]

Pitts et al.

[11] 3,972,996

[45] Aug. 3, 1976

[54] DEODORANT COMPOSITIONS CONTAINING TRANS-1,4-DIPHENYL-2-BUTENE-1,4-DIONE

[75] Inventors: Robert G. Pitts; Bruce T. Welsh, both of Morris Plains, N.J.

[73] Assignee: Warner-Lambert Company, Morris Plains, N.J.

[22] Filed: June 9, 1975

[21] Appl. No.: 585,112

[52] U.S. Cl. .................................. 424/48; 252/522; 424/49.76; 426/3; 426/660
[51] Int. Cl.$^2$ ..................... A61K 7/16; A61K 7/32; A61L 9/01; A61K 9/68
[58] Field of Search .............................. 424/48–58, 424/76; 260/590 D; 252/522; 426/3, 660

[56] References Cited
UNITED STATES PATENTS

| | | | |
|---|---|---|---|
| 2,822,254 | 2/1958 | Geopfert et al. | 51/298 |
| 3,044,939 | 7/1962 | Scanlan et al. | 424/55 |
| 3,074,892 | 1/1963 | Kulka | 424/76 X |
| 3,104,205 | 9/1963 | Hainer et al. | 424/54 |
| 3,172,817 | 3/1965 | Leupold et al. | 424/76 X |
| 3,459,852 | 8/1969 | Roehm | 424/76 |
| 3,886,265 | 5/1975 | Evers et al. | 424/49 |

OTHER PUBLICATIONS

Arctander, Perfume and Flavor Chemicals (Aroma Chemicals) I, No. 289 No. 299, No. 318, No. 319, No. 320, No. 321, No. 322, No. 638, No. 639, No. 880, No. 885, No. 1126, Pub. 1969, Arctander Montclair, N.J.

Geiger Archives of Biochemistry, vol. 16, pp. 423–435, 1948.

*Primary Examiner*—Shep K. Rose
*Attorney, Agent, or Firm*—Albert H. Graddis; Frank S. Chow; Anne M. Kelly

[57] ABSTRACT

Deodorant compositions containing from 0.01% to 0.1% by weight of trans-1,4-diphenyl-2-butene-1,4-dione by weight of the total composition are disclosed. For oral use, any suitable, non-toxic, orally acceptable formulation such as breath sprays, toothpaste, tooth powder, liquid dentifrices, liquid mouthwash, powdered mouthwash, candy products, chewing gums and the like may be used as the carrier portion of the deodorant compositions of this invention. The preferred composition is a breath spray containing about 0.05% by weight of trans-1,4-diphenyl-2-butene-1,4-dione. The trans-1,4-diphenyl-2-butene-1,4-dione deodorant ingredient may also be used directly or in a suitable formulation to eliminate various objectionable odors such as household odors caused by the presence of hydrogen sulfide and organic sulfides.

20 Claims, No Drawings

DEODORANT COMPOSITIONS CONTAINING TRANS-1,4-DIPHENYL-2-BUTENE-1,4-DIONE

BACKGROUND OF THE INVENTION

1. Field of the Invention

This invention relates to deodorant compositions containing an active deodorizing agent which may be used in the oral cavity as well as for the elimination of various other objectionable odors.

2. Description of the Prior Art

U.S. Pat. No. 2,894,876 and U.S. Pat. No. 3,044,939 describe the incorporation of copper gluconate in various compositions such as candy, chewing gum, and dental products to provide oral deodorant compositions.

U.S. Pat. No. 2,922,747 relates to oral deodorant compositions, including gums and candies, having a non-toxic lipid as the deodorizing ingredient.

U.S. Pat. No. 3,104,205 discloses an oral deodorant compositions comprising the copper complex of copolymers of allylamine and methacrylic acid. This complex is suitable for incorporation into candies, chewing gums, and dental preparations.

U.S. Pat. No. 3,459.852 relates to a process for deodorizing aqueous solutions, such as municipal and industrial wastes, sewage, stagnant water and the like, by the addition of a sulfide-active, alpha, beta-, unsaturated, aldehyde or ketone. Acrolein or 3-buten-2-one is especially recommended as the deodorizing agent.

U.S. Pat. No. 3,843,781 describes a substituted-maleimide deodorant which is sweet smelling and suitable for removing odors in lavatories, trash bins, livestock pens, and the like, caused by the presence of mercaptan and hydrogen sulfide.

SUMMARY OF THE INVENTION

Deodorant compositions and methods for eliminating malodors using such compositions are described. Oral deodorant compositions of the invention contain from 0.01% to 0.1% by weight of trans-1,4-diphenyl-2-butene-1,4-dione, based on the weight of the total composition, in a non-toxic, orally acceptable, non-reactive carrier. Suitable carriers include sugarless and sugar-containing gums and candy products; and various dental preparations such as breath sprays, toothpaste, tooth powder, liquid dentifrices, liquid mouthwash, powdered mouthwash, and the like. In addition, a method for eliminating a variety of odors by treating the odoriferous material with trans-1,4-diphenyl-2-butene-1,4-dione alone or in a suitable formulation is described.

DESCRIPTION OF THE PARTICULAR EMBODIMENTS

This invention relates to deodorant compositions containing trans-1,4-diphenyl-2-butene-1,4-dione and methods for using such compositions to substantially eliminate various malodors.

The trans-1,4-diphenyl-2-butene-1,4-dione is a known chemical intermediate which is prepared as described in J. Am. Chem. Soc. 45: 1303 (1923) and commercially available from suppliers of fine chemicals such as Aldrich Chemical Co., Milwaukee, Wisconsin and K and K Fine Chemicals Co., Plainview, New York.

According to one embodiment of this invention, the trans-1,4-diphenyl-2-butene-1,4-dione, when incorporated into a carrier suitable for use in the oral cavity at levels of from about 0.01% to about 0.1% by weight, preferably 0.05% by weight, based on the weight of the total composition, is non-toxic and effective for deodorization of the mouth. The amount of trans-1,4-diphenyl-2-butene-1,4-dione incorporated into a particular carrier material will vary somewhat depending on the dosage unit customarily used for that particular material, as will be more fully discussed below. In any event, the amount of deodorizing agent taken into the oral cavity along with the selected carrier material should be sufficient to substantially remove oral malodors within the time period that the particular carrier material is in the oral cavity.

The non-toxic, orally acceptable, non-reactive carrier materials suitable for use in the practice of this invention may be liquid or solid materials and include various confectionary compositions as well as dental preparations. Sugar-containing or sugarless confectionary materials, such as pressed tablets, boiled candies, lozenges, chewing gums or candy coated chewing gums, may be used. Representative confectionary carrier formulations appear below in the examples.

Dental preparations such as aerosol breath sprays, toothpaste, tooth powder, liquid dentifrices, liquid or powdered mouthwash formulations and the like are also envisioned as suitable carrier materials for the oral deodorant compositions of this invention. Representative dental formulations appear below in the examples.

In an aerosol breath spray containing the deodorizing agent of this invention, halogenated hydrocarbon propellants such as dichlorodifluoromethane, dichlorotetrafluoroethane and the like, or mixtures thereof, may be used. The ratio of deodorizing agent to propellant is not critical, but generally about 40% by weight of a trans-1,4-diphenyl-2-butene-1,4-dione solution and about 60% by weight of a propellant combination containing about 20% dichlorodifluoromethane and 80% dichlorotetrafluoroethane are used in the preferred breath spray product of this invention.

The trans-1,4-diphenyl-2-butene-1,4-dione deodorizing agent of this invention is a lightly colored crystalline substance, suspendable in water and soluble in organic solvents such as N,N-dimethylformamide, dimethylsulfoxide and the like; in alcohols such as ethanol and glycerol; and in vegetable oils such as peanut oil and the like.

For formulating liquid deodorant preparations of this invention, aqueous ethanol is a particularly suitable vehicle. Thus, alcohol-containing mouthwashes are indicated in order to obtain a clear, non-particulate formulation containing the trans-1,4-diphenyl-2-butene-1,4-dione dissolved therein. Aqueous base mouthwashes may be used, but the suspended trans-1,4-diphenyl-2-butene-1,4-dione deodorant particles detract from the overall appearance of the product in terms of consumer acceptance.

Alternately, powdered mouthwash formulations incorporating the solid trans-1,4-diphenyl-2-butene-1,4-dione deodorant of this invention may be easily prepared and are suitable for suspension in water at the time of use.

The trans-1,4-diphenyl-2-butene-1,4-dione deodorizing agent of this invention is stable for long periods of time in the above-mentioned orally acceptable compositions and has been found to retain its activity as an oral deodorant. Furthermore, the above-described oral deodorant compositions are non-toxic and non-irritating, when utilized in the prescribed amounts in contact with the oral cavity or when ingested. Acute oral toxicity in the hamster, mouse, rat and dog has been determined to be greater than 5000 mg/kg. In addition, cheek pouch irritation studies have indicated that the trans-1,4-diphenyl-2-butene-1,4-dione is non-irritating.

In a second embodiment of the present invention, the trans-1,4-diphenyl-2-butene-1,4-dione deodorant may be used to eliminate various objectionable odors such as those associated with diaper pails, lavatories, waste receptacles, and the like. For such uses, the active deodorizing agent may be used directly in solid or in powdered form in amounts ranging from about 0.01% to about 0.1% by weight, based on the total weight of the odoriferous material being treated. The non-toxic, non-irritating nature of the trans-1,4-diphenyl-2-butene-1,4-dione of this invention permits safe deodorization of areas and objects utilized by animals or people; the deodorizing compositions may also be used, without danger, in the presence of foods.

The trans-1,4-diphenyl-2-butene-1,4-dione of this invention may be also applied to odoriferous materials in aqueous suspensions, in an alcohol-containing liquid formulation or in aerosol form. For formulating the aerosol sprays, from about 20% to 75% of deodorizing solution is combined with from about 25% to about 80% of a propellant such as dichlorodifluoromethane and/or trichloromonoflurormethane, isobutane and the like. As has been stated above, the trans-1,4-diphenyl-2-butene-1,4-dione of this invention is compatible with a variety of formulating ingredients and has been found to remain stable and retain activity within these formulations.

Where toxicity is not a consideration, higher concentrations of the trans-1,4-diphenyl-2-butene-1,4-dione may be used to achieve deodorization within a short period of time.

Although the present invention has been described with reference to aforementioned particular embodiments, it may be extended to include similar embodiments.

The deodorizing activity of the oral compositions of the present invention has been determined by organoleptic assays as well as by gas chromographic studies which measure the presence or absence of certain volatile, odoriferous sulfur compounds such as hydrogen sulfide, methyl mercaptan, and the like. For the organoleptic assays, panels of judges skilled in making odor determinations are used to evaluate the ability of the deodorant compositions of this invention to remove odors from certain odoriferous test materials. In such assays, a base value is established for the odoriferous material, after which it is contacted with a trans-1,4-diphenyl-2-butene-1,4-dione composition of this invention. The strength and quality of odors are then evaluated by the judges, and the time required to achieve complete deodorization is measured. The deodorant compositions of this invention have been found to substantially remove malodors caused by volatile sulfides within approximately 15 minutes. Representative organoleptic assays with deodorant compositions of this invention appear below in the examples.

Although the exact process by which the trans-1,4-diphenyl-2-butene-1,4-dione deodorizing agent of this invention achieves deodorization is not known, the active ingredient is believed to react with volatile sulphur compounds solely by addition, without catalytic oxidation. It appears that the deodorizing compositions of this invention are capable of removing odoriferous monosulfides, such as hydrogen sulfide and methyl mercaptan, as well as preventing the formation of methyl disulfide.

In the gas chromographic studies, the presence of odoriferous volatile sulfides is determined by flame photometry with a 394 nm filter essentially as described by J. Tonzetich in Archives of Oral Biology, Vol. 16, pp. 587–597 (1971). According to this method, fresh saliva is incubated in a closed vial under controlled conditions. The vial is then treated with the trans-1,4-diphenyl-2-butene-1,4-dione composition of this invention and re-sealed. A sample of the head space gas above the treated saliva is then sampled and measured for the presence of volitile sulfur compounds which cause mouth odor. Results indicate that the deodorizing compositions of this invention either eliminate or significantly decrease the concentration of volitile sulfur in the head space of the test vials.

In order to further illustrate the practice of this invention, the following examples are included:

EXAMPLE 1

Effect of trans-1,4-Diphenyl-2-Butene-1,4-Dione on Putrefied Saliva

Whole saliva is collected from random donors, pooled, and 1.0 ml aliquots are added to screw cap vials of 4 dram capacity. The vials are tightly capped and incubated at 37°C. for 18 hours. An organoleptic assay is conducted using a panel of 4 judges, skilled in making odor determinations, to evaluate relative potencies of odors. Evaluations are based on a scale of 0 to 3, with 0 indicating a neutral or nearly odorless state. Initial odor measurements for putrefied saliva samples, prepared as described above, are judged to be 3.0 (maximum on the scale). After treatment of each 1.0 cc of saliva sample with 1.0 cc of a 0.1% trans-1,4-diphenyl-2-butene-1,4-dione solution in ethanol (95%), the average odor score decreased to 0.25 in 15 minutes. Control samples of putrefied saliva (1.0 cc each) with initial odor measurements of 3.0, are each treated with 1.0 cc of a 95% ethanol solution. After 15 minutes, odor measurements on controls are judged to be 2–3.

EXAMPLE 2

Effect of trans-1,4-Diphenyl-2-Butene-1,4-Dione on Garlic Odor

One milliliter of 0.005% aqueous garlic oil solution containing 0.01% ethanol and 0.01% Tween 80 was mixed with 1.0 ml of 1% trans-1,4-diphenyl-2-butene-1,4-dione in 95% ethanol. Treatments and controls were presented separately to 8 judges in a triangle test format. 100% of the judges correctly identified the TDBE-treated solutions and reported that garlic odor was essentially eliminated by treatment with the deodorizing composition of this invention.

EXAMPLE 3

Deodorant Aerosol Breath Spray Composition

A solution of 400 ml of 95% ethanol containing 250 mg of trans-1,4-diphenyl-2-butene-1,4-dione and 600 ml of a propellant containing 120 ml of dichlorodifluoromethane and 480 ml of dichlorotetrafluoroethane are added to an aerosol container and sealed. Spraying the oral cavity with this deodorant composition provides from 0.5 to 1.0 mg of trans-1,4-diphenyl-2-butene-1,4-dione in the oral cavity with each spray, customarily lasting approximately 5 seconds.

EXAMPLE 4

Deodorant Toothpaste Composition

A deodorant toothpaste was prepared from the following ingredients:

| | |
|---|---|
| Dicalcium phosphate | 40.00 gms. |
| Glycerine | 20.00 gms. |
| Carboxymethyl cellulose (medium viscosity) | 0.85 gms. |
| Sodium lauryl sulfate | 0.80 gms. |
| Heavy mineral oil | 1.00 gms. |
| Soluble saccharin | 0.07 gms. |
| trans-1,4-Diphenyl-2-butene-1,4-dione | 0.01 – 0.1 gms. |
| Distilled water, q.s. to | 100.00 gms. |

On the basis of 1 gram of toothpaste for an average "brushing", this formulation provides from 0.1 to 1.0 mg of trans-1,4-diphenyl-2-butene-1,4-dione in the oral cavity.

EXAMPLE 5

Deodorant Tooth Powder Composition

A deodorant tooth powder composition is prepared from the following ingredients:

| | |
|---|---|
| Calcium carbonate (flow rate 27) | 50.00 gms. |
| Calcium carbonate (flow rate 15) | 45.00 gms. |
| Powdered Castile soap | 4.90 gms. |
| Soluble saccharin | 0.10 gm. |
| trans-1,4-Diphenyl-2-butene-1,4-dione | 0.01 – 0.1 gms. |

On the basis of 0.6 grams of tooth powder for an average "brushing", the above formulation provides from .06 to 0.6 mg of trans-1,4-diphenyl-2-butene-1,4-dione in the oral cavity.

EXAMPLE 6

Deodorant Liquid Dentifrice Composition

A deodorant liquid dentifrice is prepared from the following ingredients:

| | |
|---|---|
| Sodium lauryl sulfate | 1.0 gms. |
| Glycerine | 8.0 gms. |
| Soluble saccharin | 0.1 gms. |
| Specially denatured alcohol | 30.0 cc. |
| Methyl cellulose | 0.6 gms. |
| trans-1,4-Diphenyl-2-butene-1,4-dione | 0.01 – 0.1 gms. |
| Distilled water, q.s. to | 100.0 cc. |

On the basis of 0.5 cc of the above liquid dentifrice for an average "brushing", from 0.05 to 0.5 mg of trans-1,4-diphenyl-2-butene-1,4-dione is provided in the oral cavity.

EXAMPLE 7

Deodorant Mouth Wash Composition

A deodorant mouth wash composition is prepared from the following ingredients:

| | |
|---|---|
| Boric acid | 2.5 gms. |
| Benzoic acid | 0.1 gms. |
| Glycerine | 2.0 gms. |
| Specially denatured alcohol | 25.0 cc. |
| trans-1,4-Diphenyl-2-butene-1,4-dione | 0.01 – 0.1 gms. |
| Distilled water, q.s. to | 100.0 cc. |

On the basis of 20 cc of mouth wash for an average "rinsing", the above formulation provides from 5 to 50 mg of trans-1,4-diphenyl-2-butene-1,4-dione in the oral cavity.

EXAMPLE 8

Deodorant Powdered Mouthwash Composition

A deodorant powdered mouthwash composition is prepared from the following ingredients:

| | | |
|---|---|---|
| Boric Acid | 1.0 | gms. |
| Benzoic Acid | 0.025 | gms. |
| Sodium Chloride | 0.10 | gms. |
| Sugar | 0.9 | gms. |
| trans-1,4-Diphenyl-2-butene-1,4-dione | 0.0025 – 0.025 | gms. |
| Flavor | Q.S. | |

About two grams of the above powdered mouthwash are dissolved in 25 ml tap water immediately before use. On the basis of 25 ml of this mouthwash for an average "rinsing", the above formulation provides from 5 to 50 mg of trans-1,4-diphenyl-2-butene-1,4-dione in the oral cavity.

EXAMPLE 9

Deodorant Pressed Candy Tablet Composition

A deodorant pressed candy tablet is prepared from the following ingredients:

| | |
|---|---|
| Sugar | 957.00 gms. |
| Glucose | 31.80 gms. |
| trans-1,4-Diphenyl-2-butene-1,4-dione | 1.0 gms. |
| Flavor | 4.00 gms. |
| Magnesium stearate | 2.86 gms. |

A single pressed tablet weighing 1.53 grams provides approximately 1.5 mg of trans-1,4-diphenyl-2-butene-1,4-dione in the oral cavity.

EXAMPLE 10

Deodorant Boiled Candy Lozenge

A deodorant boiled candy lozenge is prepared from the following ingredients:

| | |
|---|---|
| Sugar | 650 gms. |
| Corn syrup | 350 gms. |
| Flavor | 10 gms. |
| trans-1,4-Diphenyl-2-butene-1,4-dione | 1.0 gms. |

A single lozenge weighing approximately 2 grams provides 2 mg of trans-1,4-diphenyl-2-butene-1,4-dione in the oral cavity.

EXAMPLE 11

Deodorant Chewing Gum Composition

A deodorant chewing gum is prepared from the following ingredients:

| | |
|---|---|
| Gum base | 200 gms. |
| Sugar | 640 gms. |
| Corn syrup | 150 gms. |
| Flavor | 10 gms. |
| trans-1,4-Diphenyl-2-butene-1,4-dione | 0.1 – 1.0 gms. |

One piece of gum prepared from the above formulation weighing 1.0 grams provides from 0.1 to 1.0 mg of trans-1,4-diphenyl-2-butene-1,4-dione in the oral cavity.

EXAMPLE 12

Deodorant Candy Coated Chewing Gum

A deodorant candy coated chewing gum is prepared from the following ingredients:

| | |
|---|---|
| Gum Centers: | |
| Gum base | 110 gms. |
| Sugar | 340 gms. |
| Corn syrup | 110 gms. |
| Flavor | 5 gms. |
| Coating: | |
| Sugar | 427 gms. |
| Flavor | 5 gms. |
| trans-1,4-diphenyl-2-butene-1,4-dione | 1.0 gms. |

One piece of candy coated chewing gum weighing 1.75 grams provides approximately 1.75 mg of trans-1,4-diphenyl-2-butene-1,4-dione in the oral cavity.

EXAMPLE 13

Sugarless Deodorant Pressed Candy Tablet Composition

A deodorant sugarless pressed candy tablet is prepared from the following ingredients:

| | |
|---|---|
| Sorbitol | 97.621 gms. |
| Flavor | .035 gms. |
| Sweetener | 0.029 gms. |
| Magnesium stearate | 2.000 gms. |
| trans-1,4-diphenyl-2-butene-1,4-dione | 0.1 gms. |

A single pressed tablet weighing 1.5 grams provides 1.5 mg of trans-1,4-diphenyl-2-butene-1,4-dione in the oral cavity.

EXAMPLE 14

Sugarless Deodorant Chewing Gum Composition

A sugarless deodorant chewing gum is prepared from the following ingredients:

| | |
|---|---|
| Gum base | 28.00 gms. |
| Gum acacia solution (45% aqueous soltuion) | 6.00 gms. |
| Gum acacia powder | 3.00 gms. |
| Mannitol | 26.00 gms. |
| Sorbitol | 35.45 gms. |
| Flavor | 1.00 gms. |
| Sweetener | 0.14 gms. |
| Distilled water | 0.41 gms. |
| trans-1,4-diphenyl-2-butene-1,4-dione | 0.01 – 0.1 gms. |

One piece of gum prepared from the above formulation weighing 1.0 grams provides from 0.1 to 1.0 mg of trans-1,4-diphenyl-2-butene-1,4-dione in the oral cavity.

EXAMPLE 15

Anti-odor Effect of trans-1,4-Diphenyl-2-Butene-1,4-Dione Aerosol Breath Spray The inner surfaces of 3 glass jars (each providing approximately 2000 square centimeters in area) are each sprayed with 5 ml of putrefied saliva prepared as in Example 1. A control jar is sprayed with 5 ml of putrefied saliva and then an ethanol spray. The remaining test jars are then sprayed for 5 seconds with the trans-1,4-diphenyl-2-butene-1,4-dione aerosol breath spray of Example 3, to deliver approximately 250 ppm of trans-1,4-diphenyl-2-butene-1,4-dione on the inner surface of each glass jar. After several minutes have elapsed, the strong odor of the ethanol is dissipated. Using the Organoleptic Assay procedure of Example 1, the score of the control jar after treatment with ethanol spray alone, decreased from 3 to 2. The average odor score for the glass jars after treatment with the aerosol breath spray of Example 3 containing the deodorizing agent of this invention decreased from 3 to 1 in approximately 15 minutes.

EXAMPLE 16

Room Air Deodorizer

A solution of 500 ml of 95% ethanol containing 250 mg of trans-1,4-diphenyl-2-butene-1,4-dione and 500 ml of a dichlorodifluoromethane propellant are added to an aerosol container and sealed.

EXAMPLE 17

Liquid Deodorizing Formulation for Household Use

| | | |
|---|---|---|
| trans-1,4-Diphenyl-2-butene-1,4-dione | 0.1 – 1 | gms. |
| Denatured alcohol | 1000 | ml. |
| Fragrance | | Q.S. |

On the basis of 25 cc of the above for an average treatment, 2.5 – 25 mg of trans-1,4-diphenyl-2-butene-1,4-dione is provided on a treated household surface.

We claim:

1. A non-toxic deodorant composition suitable for use in the oral cavity comprising trans-1,4-diphenyl-2-butene-1,4-dione and a non-toxic, non-reactive carrier therefor, said trans-1,4-diphenyl-2-butene-1,4-dione being present in an amount effective to initiate the onset of substantial deodorization of odoriferous, volatile sulfur compounds containing mercaptans and hydrogen sulfide within approximately 15 minutes, said trans-1,4-diphenyl-2-butene-1,4-dione being present in an amount of from about 0.01% to about 0.1% by weight, based on the weight of the total composition.

2. A deodorant composition according to claim 1 wherein the trans-1,4-diphenyl-2-butene-1,4-dione is present in an amount of about 0.05% by weight.

3. A deodorant composition according to claim 1 wherein the carrier is an aerosol breath spray formulation.

4. A deodorant composition according to claim 3 wherein the trans-1,4-diphenyl-2-butene-1,4-dione is present in an amount of about 0.05% by weight.

5. A deodorant composition according to claim 1 wherein the carrier is a toothpaste formulation.

6. A deodorant composition according to claim 5 wherein the trans-1,4-diphenyl-2-butene-1,4-dione is present in an amount of about 0.05% by weight.

7. A deodorant composition according to claim 1 wherein the carrier is a tooth powder formulation.

8. A deodorant composition according to claim 7 wherein the trans-1,4-diphenyl-2-butene-1,4-dione is present in an amount of about 0.05% by weight.

9. A deodorant composition according to claim 1 wherein the carrier is a liquid dentifrice formulation.

10. A deodorant composition according to claim 9 wherein the trans-1,4-diphenyl-2-butene-1,4-dione is present in an amount of about 0.05% by weight.

11. A deodorant composition according to claim 1 wherein the carrier is a liquid, alcohol-containing mouthwash formulation.

12. A deodorant composition according to claim 11 wherein the trans-1,4-diphenyl-2-butene-1,4-dione is present in an amount of about 0.05% by weight.

13. A deodorant composition according to claim 1 wherein the carrier is a powdered mouthwash formulation which, upon the addition of water, forms a liquid suspension suitable for rinsing and deodorizing the oral cavity.

14. A deodorant composition according to claim 13 wherein the trans-1,4-diphenyl-2-butene-1,4-dione is present in an amount of about 0.05% by weight.

15. A deodorant composition according to claim 1 wherein the carrier is a candy composition.

16. A deodorant composition according to claim 15 wherein the trans-1,4-diphenyl-2-butene-1,4-dione is present in an amount of about 0.05% by weight.

17. A deodorant composition according to claim 1 wherein the carrier is a chewing gum composition.

18. A deodorant composition according to claim 17 wherein the trans-1,4-diphenyl-2-butene-1,4-dione is present in an amount of about 0.05% by weight.

19. A method for substantially eliminating mouth odors which comprises treating the oral cavity with an orally acceptable, non-toxic composition containing from about 0.01% to about 0.1% by weight, based on the weight of the total composition of trans-1,4-diphenyl-2-butene-1,4-dione, said amount being effective to initiate the onset of substantial deodorization of odoriferous volatile sulfur compounds containing mercaptans and hydrogen sulfide within approximately 15 minutes.

20. A method according to claim 19 wherein the trans-1,4-diphenyl-2-butene-1,4-dione is present in an amount of about 0.05% by weight.

* * * * *